United States Patent [19]

Omodei-Salé et al.

[11] Patent Number: 4,461,894
[45] Date of Patent: Jul. 24, 1984

[54] NAPHTH[1,2-D]IMIDAZOLES

[75] Inventors: Amedeo Omodei-Salé, Voghera; Emilio Toia, Milan, both of Italy

[73] Assignee: Gruppo Lepetit S.p.A., Milan, Italy

[21] Appl. No.: 371,768

[22] Filed: Apr. 26, 1982

Related U.S. Application Data

[62] Division of Ser. No. 230,135, Jan. 30, 1981, Pat. No. 4,360,674.

[30] Foreign Application Priority Data

Feb. 8, 1980 [GB] United Kingdom .................. 8004311

[51] Int. Cl.³ .................. C07D 403/08; C07D 487/00; A61K 31/495
[52] U.S. Cl. .................... 544/370; 544/132; 544/137; 544/360; 544/368; 546/198; 546/199; 548/217; 548/326; 424/248.4; 424/250; 424/263; 424/272; 424/273 B
[58] Field of Search .................. 544/360, 368, 370

[56] References Cited

U.S. PATENT DOCUMENTS 4,360,674 11/1982 Omodei-Salé .................... 544/370

OTHER PUBLICATIONS

Malmberg, E. W. et al., J.A.C.S., 70, 2415–2417.

Primary Examiner—Donald G. Daus
Assistant Examiner—S. A. Gibson
Attorney, Agent, or Firm—William J. Stein; Stephen L. Nesbitt; Gary D. Street

[57] ABSTRACT

Naphth[1,2-d]imidazoles and naphth[2,1-d]oxazoles of formula

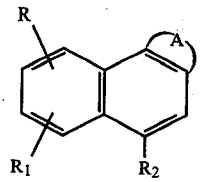

wherein R and $R_1$ are hydrogen, halogen, alkyl or alkoxy, $R_2$ is hydrogen or halogen and A is one of the following moieties

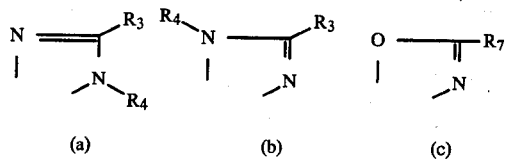

(a)  (b)  (c)

wherein $R_3$ is alkyl, cycloalkyl, or a $-(CH_2)_n NR_5 R_6$ group in which n is 1, 2 or 3, $R_5$ is hydrogen or alkyl, $R_6$ is alkyl or $R_5$ and $R_6$ taken together with the adjacent nitrogen atom are a 4- to 7-membered saturated hetero ring which may contain a further hetero atom and optionally may be substituted, e.g., with phenyl or substituted phenyl, $R_4$ is hydrogen, alkyl, cycloalkyl or a $-(CH_2)_n NR_5 R_6$ group, provided that one of $R_3$ and $R_4$ is a $-(CH_2)_n-NR_5 R_6$ group, and $R_7$ is $-(CH_2)_n-NR_5 R_6$, or a pharmaceutically-acceptable acid addition salt thereof. They are made by contacting a corresponding naphth[1,2-d]imidazole or a naphth[2,1-d]oxazole wherein one of $R_3$ and $R_4$ or $R_7$ is a $-(CH_2)_n X$ group wherein X is the residue of a reactive ester with an appropriate amine of the formula $HNR_5 R_6$ in the presence of an acid acceptor. The new compounds are useful as CNS-depressant agents.

3 Claims, No Drawings

NAPHTH[1,2-D]IMIDAZOLES

CROSS-REFERENCE TO RELATED APPLICATION

This is a divisional, of application Ser. No. 230,135, filed Jan. 30, 1981 now U.S. Pat. No. 4,360,674.

The present invention relates to new naphth[1,2-d]imidazole and naphth[2,1-d]oxazole derivatives, to the process for their preparation, to their use of C.N.S. depressant agents and to the pharmaceutical compositions containing them. More particularly the novel naphthimidazoles and naphthoxazoles of the present invention are represented by the following formula I

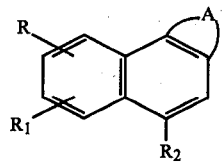

wherein R and $R_1$, each independently, are selected from the group consisting of hydrogen, halogen, ($C_1$-$C_6$)alkyl and ($C_1$-$C_6$)alkoxy; $R_2$ stands for hydrogen or halogen, and A represents one of the following moieties

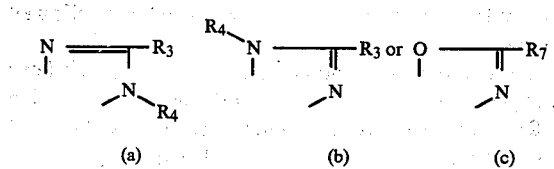

wherein $R_3$ is ($C_1$-$C_6$)alkyl, ($C_5$-$C_6$)cycloalkyl or a $(CH_2)_n$—$NR_5R_6$ group wherein n is 1, 2, or 3

$R_5$ stands for hydrogen, or ($C_1$-$C_6$)alkyl, and $R_6$ represents ($C_1$-$C_6$)alkyl or $R_5$ and $R_6$ taken together with the adjacent nitrogen atom may represent a 4- to 7-membered saturated hetero-ring which may contain a further heteroatom selected from nitrogen and oxygen, and may optionally bear a substituent selected from the group consisting of ($C_1$-$C_6$)alkyl, ($C_2$-$C_6$)alkenyl, ($C_5$-$C_6$)cycloalkyl, aliphatic-($C_2$-$C_6$)acyl, phenyl, substituted phenyl, benzyl, halo-benzyl and pyridyl, $R_4$ represent hydrogen, ($C_1$-$C_6$)alkyl, ($C_5$-$C_6$)cycloalkyl or $(CH_2)_n$—$NR_5R_6$, wherein n, $R_5$ and $R_6$ are as defined above; and $R_7$ represents a $(CH_2)_n$—$NR_5R_6$ group, wherein n, $R_5$ and $R_6$ are as defined above; with the proviso that when the symbol A represents grouping (a) or (b), one of $R_3$ and $R_4$ is a $(CH_2)_n$—$NR_5R_6$ group and with the further proviso that when $R_3$ represents a $(CH_2)_n$—$NR_5R_6$ group wherein n is 1, $R_5$ and $R_6$ taken together with the adjacent nitrogen atom may not represent a morpholino- or piperidino-radical.

A preferred group of compounds comprises those compounds of formula I wherein R, $R_1$, and $R_2$ are as defined above and the symbol A represents grouping (a) or (b), wherein $R_3$ and $R_4$ are as defined before, with the proviso that one of $R_3$ and $R_4$ is a $(CH_2)_n$—$NR_5R_6$ group.

A most-preferred group of compounds comprises those compounds of formula I wherein R and $R_1$, each independently, are selected from the group consisting of hydrogen, halogen, ($C_1$-$C_6$)alkyl, and ($C_1$-$C_6$)alkoxy, $R_2$ represents hydrogen, and the symbol A represents grouping (a) or (b), wherein $R_3$ represents ($C_1$-$C_6$)alkyl or a $(CH_2)_2$—$NR_5R_6$ group, wherein $R_5$ and $R_6$ taken together with the adjacent nitrogen atom represent a piperazine ring which may optionally bear a substituent selected from the group consisting of phenyl, substituted phenyl and pyridyl, and $R_4$ represents ($C_1$-$C_6$)alkyl or a $(CH_2)_n$—$NR_5R_6$ group wherein $R_5$ and $R_6$ are as defined above in this preferred group, with the proviso that one of $R_3$ and $R_4$ is a $(CH_2)_n$—$NR_5R_6$ group.

The term "($C_1$-$C_6$)alkyl", as used throughout the disclosure, comprehends both straight- and branched-chain hydrocarbon groups containing from 1 to 6 carbon atoms, such as methyl, ethyl, propyl, isopropyl, butyl, isobutyl, sec-butyl, tertiary butyl, pentyl, isopentyl, neopentyl, tert-pentyl, hexyl or isohexyl. Similarly, the term "($C_1$-$C_6$)alkoxy" comprehends groups such as methoxy, ethoxy, propoxy, isopropoxy, butoxy, tert-butoxy, pentyloxy, hexyloxy and the like.

Also, the term "($C_2$-$C_6$)alkenyl" comprehends straight or branched unsaturated hydrocarbon groups which may contain one or two double bonds, such as allyl, methylallyl, 1,3-butadienyl, 1,4-hexadienyl and the like. The expression "($C_5$-$C_6$)cycloalkyl" identifies a cycloalkyl radical containing 5 or 6 carbon atoms, i.e., a cyclopentyl or cyclohexyl group.

The term "($C_2$-$C_6$)aliphatic acyl" refers to an acyl radical derived from an aliphatic carboxylic acid containing 2 to 6 carbon atoms such as acetyl, propionyl, butyryl, iso-butyryl, hexanoyl and the like.

The term "substituted phenyl" designates phenyl radicals substituted with one to three groups independently selected from ($C_1$-$C_6$)alkyl, ($C_1$-$C_6$)alkoxy, hydroxy, benzyloxy, halogen, trifluoromethyl, amino, mono- and di-alkylamino and nitro.

The term "halogen" is intended to encompass all four forms thereof, i.e., chlorine, bromine, fluorine and iodine. Representative of "4 to 7-membered saturated hetero-rings" are azetidine, oxazine, pyrrolidine, piperidine, piperazine, morpholine and 1H-hexahydro-azepine.

Naphth[1,2-d]imidazoles substituted in the 2-position with a piperidinomethyl, morpholinomethyl, α-hydroxy-β-piperidino ethyl, and α-hydroxy-β-morpholinoethyl group, are known from J.A.C.S. 70, 2415-17 (1948). These compounds were studied because of possible interest as anti-malarial agents, and their syntheses were investigated and reported in the above cited literature reference.

The compounds of the present invention can be prepared according to a combination of individually known steps. The easiest and most convenient method is the nucleophilic displacement reaction of the alkyl derivatives of the formulas Ia', Ib', and Ic'

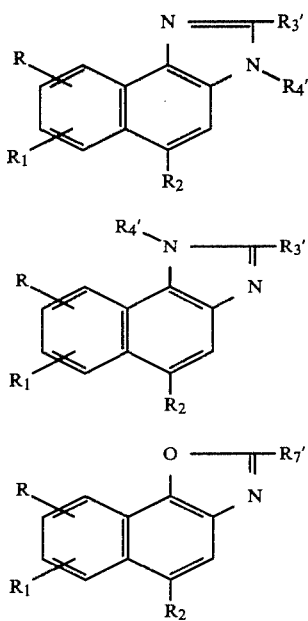

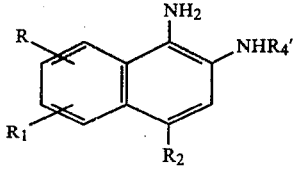

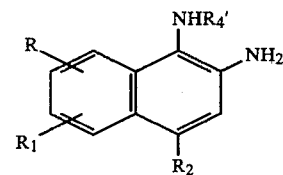

wherein
R, R₁ and R₂ have the same meanings as before,
R₃' is $(C_1-C_6)$alkyl, $(C_5-C_6)$cycloalkyl or a —$(CH_2)_n$—X group wherein n is as defined before and X is the residue of a reactive ester, especially a halogen atom such as chlorine or bromine or the residue of a sulfuric acid ester or sulfonic acid ester such as methanesulfonate, benzenesulfonate or p-toluenesulfonate,
R₄' is hydrogen, $(C_1-C_6)$alkyl, $(C_5-C_6)$cycloalkyl or a —$(CH_2)_n$—X group wherein n and X are as defined above, with the proviso that one of R'₃ and R'₄ is a —$(CH_2)_n$—X group, and
R'₇ is a —$(CH_2)_n$—X group.

This nucleophilic displacement involves the attack at carbon by a suitably-selected nucleophile HNR₅R₆ and the replacement of the leaving group —X by the group —NR₅R₆. In actual practice, the reaction is carried out by refluxing a solution of the two reactants in a polar organic solvent such as methanol, ethanol, acetonitrile, acetone, or a mixture thereof, and the like, under an inert atmosphere for several hours. In order to remove the hydrohalic, sulfuric or sulfonic acid which forms during the reaction, a double molar amount of the amine HNR₅R₆ is preferably employed; alternatively, or in addition, other basic agents, such as alkali or alkaline earth metal carbonates, hydroxides or lower alkoxides, or organic nitrogen bases such as pyridine, collidine or aliphatic tertiary amines, can be employed. The end products of formula I are then recovered by evaporating the solvent and are roughly pufified by washing with water. Finally, crystallization from a suitable solvent or column chromatography, or both, afford the purified end products. Both starting compounds may be employed as free bases or as the corresponding acid addition salts, typically as the hydrochlorides; in this case a further amount of basic agent has obviously to be employed.

For practical reasons when compounds of formula I are prepared wherein the symbol A represents grouping (a) or (b) wherein R₃ represents —$(CH_2)_n$—NR₅R₆ and R₄ is hydrogen $(C_1-C_6)$alkyl, or $(C_5-C_6)$cycloalkyl, starting compounds of the above formulas Ia' and Ib' are preferably employed wherein the symbol X represents a halogen atom, such as chlorine or bromine, since they may be easily prepared from the corresponding diaminonaphthalene derivatives of formulas IIa and IIb respectively

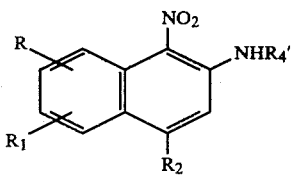

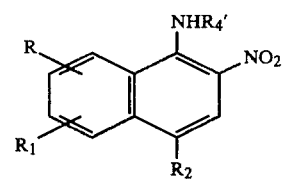

through condensation with a suitably selected acyl chloride of the formula

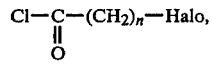

wherein Halo represents chlorine, or bromine, followed by cyclization.

If desired, the cyclization reaction may be carried out in the presence of at least the molar amount of the amine HNR₅R₆ and a hydrogen halide acceptor, as defined before, yielding directly the desired end products of formulas Ia and Ib wherein R₄ is hydrogen, $(C_1-C_6)$alkyl, or $(C_5-C_6)$cycloalkyl, and R₃ is a —$(CH_2)_n$—NR₅R₆ group.

The diamino derivatives IIa and IIb are known or may be prepared by reducing the corresponding nitro compounds, IIIa and IIIb, respectively which in their turn may be prepared by conventional procedures well known in organic chemistry.

Another method for preparing the diamino derivatives IIa is represented by the reduction of the corresponding 1-nitroso-N-substituted-naphthaleneamines obtained according to the method described by S. T. Morgan and F. P. Evens in J. Chem. Soc. 115, 1140 (1919), through acid-catalyzed rearrangement of a 2-(N-nitroso-N-substituted)naphthyl-amine or more conveniently through reaction of a primary amine with 1- nitroso-2-naphthol according to E. W. Malmberg and C. S. Hamilton, J. Am. Chem. Soc. 70, 2415 (1948). A different route for preparing starting compounds of formulas Ia' and Ib' wherein R'$_3$ is a —(CH$_2$)$_n$—Halo group and R'$_4$ is hydrogen, alkyl, or cycloalkyl, involves the condensation of the acyl chloride the symbol X stands for a sulfonate group. In fact, the process for preparing the starting compounds Ib', which is described in the following scheme, leads to the formation of the corresponding alcohols which are conveniently activated by conversion to sulfonate esters through reaction with a sulphonyl chloride as known in the art.

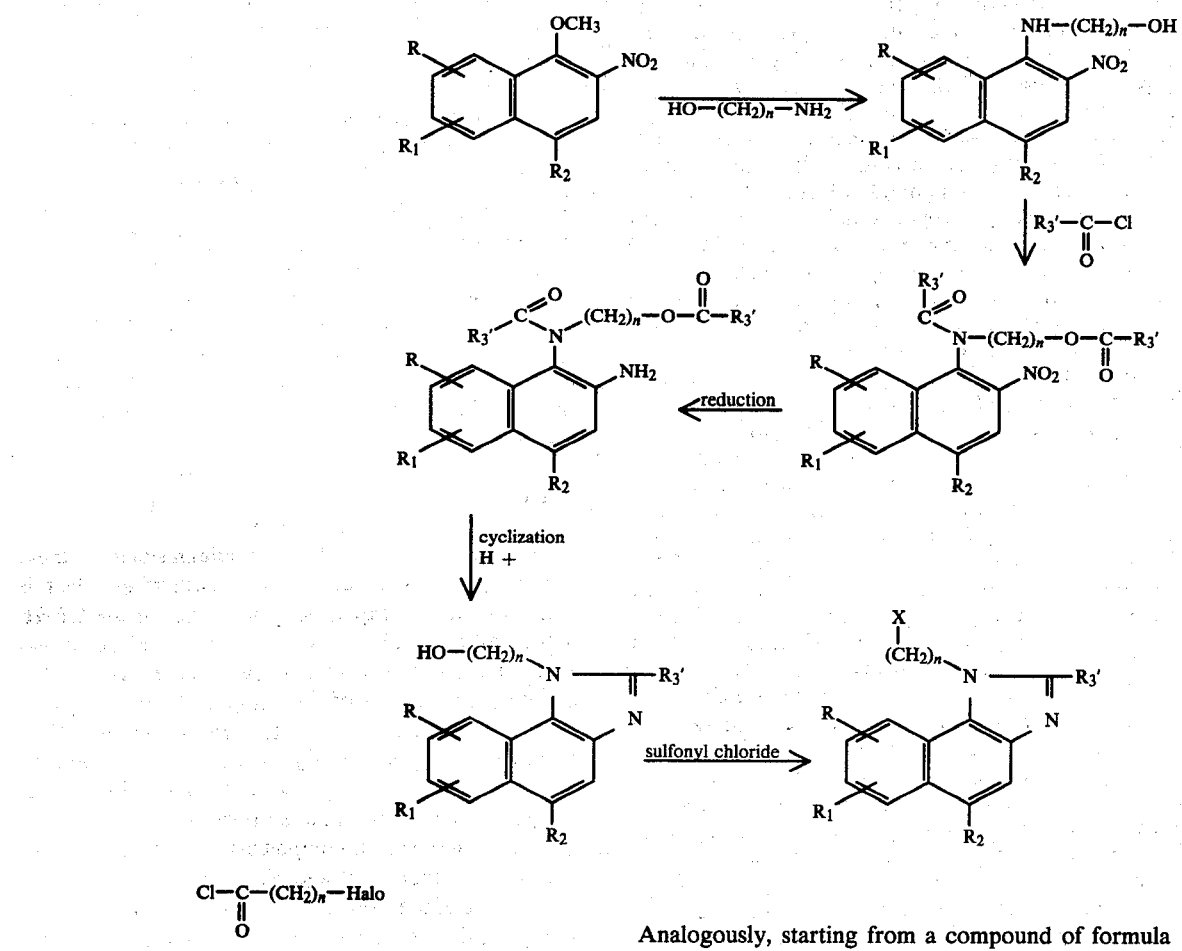

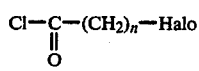

with one of the derivatives IIIa and IIIb, followed by reduction of the nitro group to amino and simultaneous cyclization. Depending on the meanings of the radical R$_2$, different reducing agents may be employed. As an example, when R$_2$ is hydrogen, the nitro group may be reduced through catalytic hydrogenation with hydrogen in the presence of a catalyst, such as platinum or palladium, preferably adsorbed on charcoal, or Raney nickel. Milder agents and conditions, such as, for instance, iron in acetic acid, have to be employed when R$_2$ is a halogen atom, in order to avoid hydrogenolysis of this group. Also in this case when preparing starting compounds of formula Ia' the condensation may be carried out between the acyl chloride

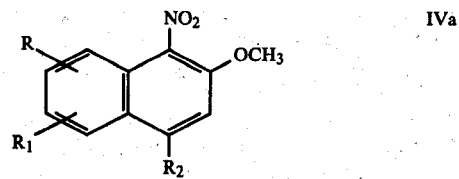

Analogously, starting from a compound of formula IVa and following the same process, the starting compounds of formula Ia' are obtained. Finally, starting compounds of formula Ic' wherein X is a halogen atom are prepared from the corresponding 2-amino-1-hydroxy-naphthalene derivatives through condensation with

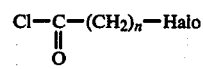

followed or accompanied by ring closure to naphthoxazole. Another method for preparing compounds of formula I wherein independently from the meanings of R, R$_1$ and A, R$_2$ is a hydrogen atom, is represented by the hydrogenolysis of the corresponding compounds and the suitably-selected 1-nitroso-N-substituted-2-naphthaleneamine derivative. When compounds of formula Ib are desired wherein R$_3$ is alkyl or cycloalkyl and R$_4$ is a —(CH$_2$)$_n$—NR$_5$R$_6$ group, starting compounds of formula Ib' are preferably employed wherein wherein $R_2$ is halogen. Said hydrogenolysis can be carried out by means of hydrogen in the presence of a catalyst or by means of alkali metal aluminium hydrides. The catalytic reduction with hydrogen is preferably performed at ambient temperature, and at a pressure ranging from atmospheric pressure to about 10 atmospheres. The catalysts employed are selected from the usual hydrogenation catalysts such as Pt, Pd, Ru, Rh, preferably adsorbed on a carrier. Representative of the alkali metal aluminium hydrides which may suitably be employed are $LiAlH_4$, $NaAl-(OCH_2-CH_2OCH_3)_2H_2$ and $LiAlH(OCH_3)_3$. The novel naphthoimidazoles and naphthoxazoles of formula I form acid addition salts. These acid addition salts are obtained by treating a compound of formula I above with a pharmaceutically acceptable acid. As acids suitable for formation of therapeutically acceptable salts there may be mentioned, for example, hydrohalic, sulfuric, phosphoric and nitric acid; aliphatic, alicyclic, aromatic or heterocyclic carboxylic or sulfonic acids, such as formic, acetic, propionic, succinic, aspartic, glycolic, gluconic, lactic, malic, tartaric, citric, ascorbic, maleic, hydroxymaleic, and pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethane-sulfonic and ethylenesulfonic acid; halobenzenesulfonic, toluenesulfonic, naphthalenesulfonic and sulfanilic acid. These or other salts of the new compounds may also be used for purifying the resulting compounds by converting them into salts, isolating the latter and liberating the free compound from them. In view of the close relationship between the new compounds in the free form and in the form of their salts what has been said above and hereinafter with reference to the free compounds concerns also the corresponding salts. The novel naphthimidazoles and naphthoxazoles of the present invention are valuable medicinal agents and in particular they are useful as CNS-depressant agents. This activity has been assessed by observing the behavioural and neurological changes they induce in normal mice, by means of a multifactorial observational technique similar to that originally developed by Irwin and described in Psycho-pharmacologia (Berl.) 13, 222–257 (1968). The general procedure used in said tests however is a simplified one wherein the number of parameters evaluated and scored is reduced with respect to the original method. (See C. Morpurgo-Arzneim-Forsh. (Drug Res.) 21, 1727 (1971). In particular, representative test compounds are administered intraperitoneally in increasing doses to groups of three mice each and the animals are observed over 8 hours following the treatment, for the assessment of potential CNS-activity; the signs which are noted and scored are a diminution of the spontaneous exploratory activity, a diminution of the spontaneous locomotor activity, disturbances in the motor coordination (Ataxia) and relaxation. A range of 0 to 4 scoring is arbitrarily employed which is intended to represent the average intensity of the phenomenon observed (score 0 expresses the normal behaviour in respect to controls and an increase in score is used to quantify the observed depressant activity). The animals are also observed twice a day for 5 days following the treatment to evaluate toxicity, and the approximate $LD_{50}$ values, i.e., the dosages which are lethal to 50 percent of the mice, are calculated from the mortality within 120 hours after administration. The results obtained in these screening tests showed that doses ranging from 1/10 to 1/5 of the corresponding $LD_{50}$s of the compounds of representative examples 1,4,5,6,9,10,11, 12, 14, 15, 24, 27, 31, 32, 33, 34, and 35 are fully effective in depressing the central nervous system, producing a marked increase in the scores for all the above four signs of CNS-depression.

Moreover, the activity of some representative compounds of the present invention has been tested also upon conditioned responses in rats according to the method described by Cook and Weidley in Ann. N.Y. Acad. Sci. 1957, 66, 740 and subsequently modified by Maffii (J.Pharm. and Pharmacol., 1959, 11, 129–139). In this procedure a rat is placed in a chamber with a grid floor through which electric shocks may be delivered. This chamber is also equipped with a buzzer and with a wooden pole, electrically isolated, which is suspended from the top of the experimental chamber. The animal soon learns to escape the shock by climbing the pole (unconditioned response-U.R.) and by climbing the pole in response to the buzzer alone (conditioned avoidance response-CR). After further exposure to the situation, the rat becomes conditioned and climbs the pole before the buzzer is activated; when this response becomes stable the rat is considered to have developed a secondary conditioned response ($CR_2$).

The drug to be studied is then administered to these long-trained animals and its deconditioning effect is evaluated. In our experiments male rats of the CFHB Wistar strain, weighing 200–450 g were used, and it was found that doses of between about 1/20 and 1/10 of the corresponding $LD_{50}$s of the compounds of examples 1 and 10 when adminstered intraperitoneally, are effective in inhibiting completely the secondary conditioned and the conditioned responses ($CR_2$ and CR) without influencing and unconditioned response.

The use of the novel compounds of the present invention as CNS-depressant agents, which is a further specific object of the present invention, refers to all industrially applicable aspects and acts of said use, including the embodiment of the novel compounds or their acid addition salts into pharmaceutical compositions. Suitable pharmaceutical preparations contain the novel compounds or their pharmaceutically-acceptable acid addition salts in admixture or conjunction with organic or inorganic, solid or liquid pharmaceutical excipients and may be employed for enteral and parenteral administration. Suitable excipients are substances that do not react with the new compounds, e.g., water, gelatin, lactose, starches, magnesium stearate, talcum, vegetable oils, benzyl alcohols, polyalkylene-glycols or other known medicinal excipients. The new compounds may be administered by various routes; orally subcutaneously, intramuscularly or intravenously, for example. For oral administration, the substances are compounded in such forms as tablets, dispersible powders, capsules, granules, syrups, elixirs and solutions. For intravenous or intramuscular administration, the active ingredients are embodied in injectable dosage forms. Such compositions are formulated as known in the art. The following examples describe in detail representative compounds of formula I and illustrate the process for preparing them without limiting the scope of the invention.

EXAMPLE 1

1-methyl-2-[2-(4-phenyl-1-piperazinyl)ethyl]-1-H-naphth[1,2,-d]imidazole 4.22 g (0.017 mole) of 2-(2-chloroethyl)-1-methyl-1H-naphth[1,2-d]imidazole and 5.44 cc (0.035 mole) of 97% 1-phenylpiperazine are dissolved in 90 cc of anhydrous acetonitrile and the so obtained reaction mixture is refluxed with stirring under a nitrogen atmosphere. After 26 hours, 1 cc (0.006 mole) of 1-phenylipiperazine is added and refluxing is prolonged for 8 additional hours. After evaporating the solvent, the resulting residue is taken up with a small amount of water, filtered and dried. Crystallization from ethyl acetate affords 5.06 g (79% yield) of the compound of the title which melts at 139°-141° C.

6.6 g (0.0 178 mole) of the compound of the title is dissolved in 300 cc of hot methanol and treated with a solution of 3.74 g (0.0178 mole) of citric acid monohydrate in 50 cc of methanol. Upon cooling to 0° C., 9.30 g of 1-methyl 2-[2-(4-phenyl-1-piperazinyl)ethyl]-1H-naphth-[1,2-d]imidazole citrate crystallizes out. (Yield 93%). M.p. 190° C. with decomposition.

Treatment of equimolecular amounts of the compound of the title and methanesulfonic acid affords the 1-methyl-2-[2-(4-phenyl-1-piperazinyl)ethyl]-1H-naphth[1,2-d]imidazole mesylate which melts at 175°-177° C.

EXAMPLES 2 TO 8

With the same procedures employed for preparing the compound of Example 1 the following compounds are obtained (the starting materials are indicated between brackets):

2—1-methyl-2-[2-(4-morpholinyl)ethyl[-1H-naphth[1,2-d]imidazole. M.p. 161°-163° C.
  [from 2-(2-chloroethyl)-1-methyl-1H-naphth[1,2-d]imidazole and morpholine]
3—2-[2-(diethylamino)ethyl]-1-methyl-H-naphth[1,2-d]imidazole. M.p. 81°-82° C.
  [from 2-(2-chloroethyl)-1-methyl-1H-naphth[1,2-d]imidazole and diethylamine]
4—5-bromo-1-butyl-2-[2-(4-phenyl-1-piperazinyl)ethyl]-1H-naphth[1,2-d]imidazole. M.p. 132°-34° C.
  [from 5-bromo-1-butyl-2-(2-chloroethyl)-1H-naphth[1,2-d]imidazole and 1-phenylpiperazine]
5—2-[2-(4-phenyl-1-piperazinyl)ethyl]naphth[2,1-d]oxazole. M.p. 120°-21° C. (EtOH)
  (from 2-chloroethyl-naphth[2,1-d]oxazole and 1-phenylpiperazine)
6—1-methyl 2-[3-(4-phenyl-1-piperazinyl)propyl]-1H-naphth[1,2,-d]imidazole, M.p. 140°-41° C. (ethyl acetate)
  (from 2-(3-chloropropyl)-1-methyl-1H-naphth[1,2-d]imidazole and 1-phenylpiperazine)
7—2-[2-(4-acetylpiperazinyl)ethyl]-5-bromo-1-methyl-1H-naphth[1,2-d]imidazole
  (from 5-bromo-2-(2-chloroethyl)-1-methyl-1H-naphth[1,2-d]imidazole hydrochloride and 1-acetylpiperazine hydrochloride)
8—2-[(4-phenyl-1-piperazinyl)methyl]-1-methyl-1H-naphth-[1,2-d]imidazole M.p. 197°-198° C. (EtOH)
  (from 2-chloromethyl-1-methyl-1H-naphth[1,2-d]imidazole hydrochloride and 1-phenylpiperazine).

EXAMPLE 9

1-Methyl-2-[2-[4-(2-methoxyphenyl)piperazinyl]-ethyl]-1H-naphth[1,2-d]imidazole hydrate 2.6 g (0.013 mole) of 97% 1-(2-methoxyphenyl)-piperazine and 1.3 g (0.013 mole) of ground $KHCO_3$ are added to a solution of 2.93 g (0.012 mole) of 2-(2-chloroethyl)-1-methyl-1H-naphth[1,2-d]imidazole in 100 cc of anhydrous alcohol, maintained under an argon atmosphere. The obtained reaction mixture is refluxed with stirring under argon, and three 1.3 g portions of 97% 1-(2-methoxyphenyl)piperazine are added at the $23^{rd}$, 30th and $43^{rd}$ hour of refluxing. After 50 hours, the solvent is evaporated and the residue is taken up with a small amount of water, filtered and dried, yielding 5.1 g of raw material. Crystallization from a mixture of 160 cc of water and 140 cc of ethanol affords 4.55 g of pure compound melting at 154°-55° C. (Yield 90%)

EXAMPLES 10 TO 13

By following essentially the same procedure described in the foregoing example, but substituting the condensation of 2-(2-chloroethyl)-1-methyl-1H-naphth[1,2-d]imidazole with a suitably-selected amine in the presence of potassium bicarbonate as the hydrogen halide acceptor, the following compounds are obtained:

10—2-[2-[4-(3-methoxyphenyl)piperazinyl]ethyl]-1-methyl-1H-naphth[1,2-d]imidazole hemihydrate. M.p. 134°-36° C. (EtOH/H2O). The corresponding citrate melts at 154°-56° C. (from mehanol)
11—2-[2-[4-(4-methoxyphenyl)piperazinyl]ethyl]-1-methyl-1H-naphth[1,2-d]imidazole. M.p. 201°-202° C. (EtOH). The corresponding citrate melts at 192° C. with decomposition (from ethanol).
12—2-[2-[4-(2-chlorophenyl)piperazinyl]ethyl]-1-methyl-1H-naphth[1,2-d]imidazole. M.p. 159°-161° C. (EtOAc)
13—1-methyl-2-[2-[4-(2-pyridinyl)piperazinyl]ethyl]-1H-naphth[1,2-d]imidazole. M.p. 150°-151° C. (EtOAc)

EXAMPLE 14

2-[2-[4-(3-chlorophenyl)piperazinyl]ethyl]-1-methyl-1H-naphth[1,2-d]imidazole 6.5 g (0.024 mole) of 1-(3-chlorophenyl)piperazine dihydrochloride and 8.43 cc (0.06 mole) of triethylamine are added to a solution of 2.93 g (0.012 mole) of 2-(2-chloroethyl)-1-methyl-1H-naphth[1,2-d]imidazole in 100 cc of 95% ethanol. The obtained reaction mixture is refluxed under an argon atmosphere for 34 hours, then the solvent is evaporated, the residue is taken up with a small amount of water and filtered, yielding 5.04 g of raw product.

Purification, achieved by silica gel column chromatography using $CHCl_3$:MeOH 99:1 as the eluting system, and recrystallization from ethyl acetate, yields 3.91 g of pure compound melting at 146°-148° C. By adding a solution of hydrogen chloride in ethyl ether to a solution of the free base in the same solvent, the corresponding dihydrochloride crystallizes out. M.p. 185°-87° C.

EXAMPLE 15

2-[2-[4-(4-chlorophenyl)piperazinyl]ethyl]-1-methyl-1H-naphth[1,2-d]imidazole 6.5 g (0.024 mole) of 1-(4-chlorophenyl)-piperazine dihydrochloride and 8.43 cc (0.06 mole) of triethylamine are added to a solution of 2.93 g (0.012 mole) of 2-(2-chloroethyl)-1-methyl-1H-naphth[1,2-d]imidazole in 100 cc of ethanol. The reaction mixture is then heated at reflux temperature and maintained under an argon atmosphere for 23 hours. By evaporating the solvent, grinding the residue with water and filtering, a raw product is obtained, which is recrystallized from methylisopropylketone, yielding 4.36 g (90% yield) of pure compound. M.p. 213°–15° C.

EXAMPLE 16

5-Bromo-2-[2-(4-benzyl-1-piperazinyl)ethyl]-1-methyl-1H-naphth[1,2-d]imidazole 4 cc (0.022 mole) of 1-benzylpiperazine is added to a solution of 7.2 g (0.02 mole) of 5-bromo-2-(2-chloroethyl)-1-methyl-1H-naphth[1,2-d]imidazole hydrochloride and 40 cc (0.04 mole) of 1N NaOH in 100 cc of hot methanol, and the obtained reaction mixture is heated under an argon atmosphere at reflux temperature for several hours. When the reaction, which is followed by thin layer chromatography, is completed, the solvent is boiled off and the obtained residue is taken up with a small amount of water, filtered and dried. Yield 8.87 g. M.p. 155°–157° C.

EXAMPLE 17

5-Bromo-1-methyl-2-[2-(4-phenylpiperidinyl)ethyl]-1H-naphth[1,2-d]imidazole

The compound of the title is prepared by condensing 5-bromo-2-(2-chloroethyl)-1-methyl-1H-naphth[1,2-d]imidazole hydrochloride with 4-phenylpiperidine according to the method described in the foregoing example. M.p. 182°–84° C.

EXAMPLE 18

5-Bromo-1-methyl-2-[2-(4-methyl-1-piperazinyl)ethyl]-1H-naphth[1,2-d]imidazole

By following the procedure described in Example 16 but using 1-methylpiperazine instead of 1-benzylpiperazine, the compound of the title is obtained. M.p. 151°–157° C. (from acetone)

EXAMPLE 19

5-Bromo-1-methyl-2-[2-[4-(3-methylpheny)-1-piperazinyl]ethyl]-1H-naphth[1,2-d]imidazole By following the procedure described in Example 16 but using 1-(3-methylphenyl)piperazine instead of 1-benzylpiperazine, the compound of the title is obtained. M.p. 155°–157° C. (from ethyl acetate).

EXAMPLE 20

5-Bromo-1-methyl-2-[2-[4-(3-trifluoromethylphenyl)-1-piperazinyl]ethyl]-1H-naphth[1,2-d]imidazole The compound of the title is prepared by condensing 5-bromo-2-(2-chloroethyl)-1-methyl-1H-naphth[1,2-d]imidazole hydrochloride with 1-(3-trifluoromethyl)-piperazine according to the method described in Example 16. M.p. 165°–166° C. (from ethanol).

EXAMPLE 21

5-Bromo-1-(1-methylethyl)-2-[2-(4-phenyl-1-piperazinyl)ethyl]-1H-naphth[1,2-d]imidazole By following the procedure described in Example 16 but condensing 5-bromo-2-(2-chloroethyl)-1-(1-methylethyl)-1H-naphth[1,2-d]imidazole hydrochloride with 1-phenylpiperazine, the compound of the title is obtained. M.p. 211°–213° C. (from ethyl acetate). The corresponding citrate melts at 169°–171° C. with decomposition.

EXAMPLE 22

5-Bromo-1-(1-methylethyl)-2-[2-[4-(3-methoxyphenyl)-1-piperazinyl]ethyl]-1H-naphth[1,2-d]imidazole The compound of the title is obtained by condensing 5-bromo-2-(2-chloroethyl)-1-(1-methylethyl)-1H-naphth[1,2-d]imidazole hydrochloride with 1-(3-methoxyphenyl)piperazine according to the procedure described in Example 16. M.p. 144°–147° C. (from methanol).

EXAMPLE 23

5-Bromo-1-(1-methylethyl)-2-[2-[4-(3-trifluoromethylphenyl)-1-piperazinyl]ethyl]-1H-naphth[1,2-d]imidazole The compound of the title is prepared by condensing 5-bromo-2-(2-chloroethyl)-1-(1-methylethyl)-1H-naphth[1,2-d]imidazole hydrochloride with 1-(3-trifluoromethylphenyl)piperazine. M.p. 161°–162° C. (from ethanol).

EXAMPLE 24

2-Methyl-1-[2-(4-phenyl-1-piperazinyl)ethyl]-1H-naphth[1,2-d]imidazole 10.85 g (0.0356 mole) of 2-[2-methyl-naphth[1,2-d]imidazole-1-yl]ethyl methanesulfonate is dissolved in 200 cc of acetonitrile and 13.1 cc (0.078 mole) of 4-phenyl-1-piperazine are added to the obtained solution. After heating the reaction mixture at reflux temperature for 1½ hour, the solvent is boiled off and the residue is heated at 130° C. for 3 hours. Then the resulting product is taken up with methylene chloride, washed with water, dried over MgSO4, filtered through a layer of neutral alumina and concentrated to dryness. After two recrystallizations of the dried product from ethyl acetate, 7.8 g of the compound of the title was obtained. M.p. 182°–183° C.

6.6 g (0.0178 mole) of the compound thus obtained is dissolved in 300 cc of hot methanol and treated with a solution of 3.74 g of citric acid monohydrate in 50 cc of methanol. Upon cooling to 0° C., a solid crystallizes out which is separated by filtration. Yield 9.3 g (92.8%). M.p. 138° C. (dec.).

EXAMPLE 25

2-[2-(4-benzyl-1-piperazinyl)ethyl]-1-methyl-1H-naphth[1,2-d]imidazole 3.9 cc of toluene containing 2.62 g (0.013 mole) of (CH$_3$OCH$_2$CH$_2$O)$_2$NaAlH$_2$ is added to a solution of 4.13 g (0.0089 mole) of the compound of Example 16 in 80 cc of toluene and the obtained mixture is refluxed with stirring under argon atmosphere. After 6 hours, when the reaction, which is followed by thin layer chromatography, is completed, 100 cc of 5% NaOH is added to the mixture and the toluene phase is separated and washed with a saturated NaCl solution. Upon evaporating the solvent, a crude product is obtained which is recrystallized from ethyl acetate:hexane 1:1, yielding 2 g of the compound of the title. M.p. 144°–46° C.

EXAMPLE 26

1-Methyl-2-[2-(4-phenyl-1-piperidinyl)ethyl]-1H-naphth[1,2-d]imidazole

A mixture of 8.32 g (0.0185 mole) of the compound of Example 16, 0.9 g of 10% Pd-C catalyst, and 150 cc of tetrahydrofuran containing 20 cc of 1M NaOH is shaken in a Paar hydrogenator under about 5.4 atm. of hydrogen pressure until hydrogenolysis is completed. The catalyst is filtered and the mother liquor is concentrated to remove the solvent. The residue is taken up with methylene chloride, and washed with water. Upon evaporating the solvent, 6.1 g of a crude product are obtained which is recrystallized from acetone yielding 4.74 g of the compound of the title. M.p. 181.5°–182.5° C.

EXAMPLES 27 TO 33

By operating according to the procedures described in the foregoing examples but starting from the corresonding bromo derivatives which are described in Examples 4, 7, 18, 19, 20, 22, and 23, respectively, the following compounds are obtained:
- 27—1-butyl-2-[2-(4-phenyl-1-piperazinyl)ethyl]-1H-naphth[1,2-d]imidazole. M.p. 93°–95° C.
- 28—2-[2-(4-acetyl-1-piperazinyl)ethyl]-1-methyl-1H-naphth[1,2-d]imidazole. M.p. 152°–54° C.
- 29—1-methyl-2-[2-(4-methyl-1-piperazinyl)ethyl]-1H-naphth[1,2-d]imidazole. M.p. 118°–121° C.
- 30—1-methyl-2-[2-[4-(3-methylphenyl)-1-piperazinyl]ethyl]-1H-naphth[1,2-d]imidazole. M.p. 165°–167° C. with decomposition (from methanol).
- 31—1methyl-2-[2-[4-(3-trifluoromethylphenyl)-1-piperazinyl]ethyl-1H-naphth[1,2-d]imidazole. M.p. 144°–145° C. with decomposition (from methanol).
- 32—1-(1-methylethyl)-2-[2-[4-(3-methoxyphenyl)-1-piperazinyl]ethyl]-1H-naphth[1,2-d]imidazole citrate. M.p. 144°–47° C. (from methanol).
- 33—1-(1-methylethyl)-2-[2-[4-(3-trifluoromethylphenyl)-1-piperazinyl]ethyl]-1H-naphth[1,2-d]imidazole citrate. M.p. 144°–145° C. with decomposition (from methaol).

EXAMPLE 34

3-Methyl-2-[2-(4-phenyl-1-piperazinyl)ethyl]-3H-naphth[1,2-d]imidazole

A solution of 5.25 g (0.02 mole) of N-(1-amino-2-naphthyl)-3-chloro-N-methyl-propanamide in 150 cc of anhydrous benzene is gradually added to a solution of 9.73 g (0.06 mole) of 1-phenylpiperazine in 25 cc of anhydrous benzene under argon atmosphere over a period of time of twenty minutes. The reaction mixture is then refluxed for 21 hours. Further, 11.73 g (0.0724 mole) of 1-phenylpiperazine is added and reflux is continued for an additional 24 hours. After cooling to room temperature, the mixture is diluted with 350 cc of benzene, poured into a separatory funnel and washed with 100 cc of water containing 7.8 cc of acetic acid. The benzene phase is extracted four times with 40 cc portions of 8% HCl. The pH of the aqueous acid phase is brought to 9 by addition of concentrated NH$_4$OH and this aqueous solution is extracted with methylene chloride. The organic extracts are combined, dried over Na$_2$SO$_4$, filtered and evaporated to dryness yielding 4.03 g of raw compound which is recrystallized from 25 cc of ethanol. M.p. 153°–155° C.

EXAMPLE 35

2-[2-(4-phenyl-1-piperazinyl)ethyl]naphth[1,2-d]imidazole 7.8 cc (0.05 mole) of 97% 1-phenyl-piperazine is added to a solution of 5.21 g (0.0226 mole) of 2-(2-chloroethyl)naphth[1,2-d]imidazole in 60 cc of methanol.

The mixture is heated at reflux temperature (methanol is boiled off) and the obtained residue is maintained at 130° C. for 1½ hour. The residue is cooled and taken up with water and methylene chloride. The organic layer is separated, dried over MgSO$_4$, filtered and concentrated to dryness. The product (9.9 g) is purified by silica gel column chromatography, eluting with CHCl$_3$:CH$_3$OH 95:5. The yield of 2-[2-(4-phenyl-1-piperazinyl)ethyl]naphth[1,2-d]imidazole, M.p. 115°–117° C., (from ethyl acetate), is 4 g (49.7%).

By operating according to the procedures described in the foregoing examples, the following compounds can be prepared:
- 2-methyl-3-[2-(4-phenyl-1-piperazinyl)ethyl]-3H-naphth[1,2-d]imidazole
- 1-methyl-2-[2-[4-(4-methylphenyl)-1-piperazinyl]ethyl]-1H-naphth[1,2-d]imidazole
- 1-methyl-2-[2-[4-(2-methylphenyl-1-piperazinyl]ethyl]-1H-naphth[1,2-d]imidazole
- 1-methyl-2-[2-[4-(4-trifluoromethylphenyl)-1-piperazinyl]ethyl]-1H-naphth[1,2-d]imidazole
- 1-methyl-2-[2-[4-cyclopentyl-1-piperazinyl]ethyl]-1H-naphth[1,2-d]imidazole
- 3-methyl-2-[2-[4-(3-trifluoromethylphenyl)-1-piperazinyl]ethyl-3H-naphth[1,2-d]imidazole
- 1-pentyl-2-[2-(4-phenyl-1-piperazinyl)ethyl]-1H-naphth-[1,2-d]imidazole
- 3-hexyl-2-[2-(4-phenyl-1-piperazinyl)ethyl]-3H-naphth-[1,2-d]imidazole Preparation of the starting materials.

EXAMPLE 36

2-(2-Chloroethyl)-1-methyl-1H-naphth[1,2-d]imidazole 1.1 cc (0.012 mole) of a 35% aqueous solution of CH$_3$NH$_2$ is gradually dripped into a stirred solution of 2.82 g (0.01 mole) of 4-bromo-1-methoxy-2-nitronaphthalene in 20 cc of dimethylformamide heated to 60° C. The reaction mixture is stirred at 60° C. for 10 minutes then cooled to 0° C. and filtered, yielding 1.81 g of 4-bromo-N-methyl-2-nitro-1-naphthylamine. Further, an addtional 0.79 g of this compound is obtained from the mother liquors by dilution with water. Overall yield 92%. M.p. 187°–188° C. (from Ethanol). A mixture of 35.3 g (0.1255 mole) of 4-bromo-N-methyl-2-nitro-1-naphthylamine, 1.8 g of 10% Pd-C catalyst, and 600 cc of methanol containing 17.6 cc (0.1255 mole) of triethylamine is shaken in a Paar hydrogenator under about 5 atm. of hydrogen pressure for 1½ hours, until the theoretical amount of hydrogen is adsorbed, then the catalyst is filtered off under argon atmosphere and the mother liquor is concentrated to dryness. The residue is taken up with 250 cc of benzene and filtered again under argon over celite and bleaching earth FF. By evaporating the solvent, 19.73 g (0.115 mole) of $N^1$-methyl-1,2-naphthyldiamine is obtained as a dark oil. To a mixture of this compound and 16.1 cc (0.115 mole) of triethylamine in 500 cc of methylene chloride cooled to 0°–5° C. and kept under argon atmosphere, a solution of 14.55 g (0.115 mole) of 3-chloropropanoyl chloride in 140 cc of anhydrous methylene chloride is added dropwise. When the addition is terminated, the reaction mixture is allowed to stand at room temperature for a few hours and then it is heated at reflux temperature for ½ hour. The pH is brought to 7 by the addition of 2 cc of triethylamine and the reaction mixture is warmed to 35° C. for two hours, washed with water and dried. The raw product (25.5 g) which is obtained by evaporating the solvent is taken up with 160 cc of 5% HCl and stirred at 60° C. for 3 hours. The solids which are insoluble at this temperature are separated by filtration and discarded while the solution is decolorized with activated carbon. The clear solution is cooled to 0° C. and made alkaline with NH$_4$OH. The product which precipitates is separated by filtration and recrystallized from 95% Ethanol. Yield 57.6%. M.p. 251° C. (dec.).

EXAMPLE 37

5-Bromo-1-butyl-2-(2-chloroethyl)-1H-naphth[1,2-d]imidazole 7.05 g (0.025 mole) of 4-bromo-1-methoxy-2-nitronaphthalene is dissolved in 300 cc of methanol by heating the mixture at reflux temperature, then 5 cc (0.05 mole) of butylamine is gradually dripped into the obtained solution and when the addition is terminated the reaction mixture is still refluxed for 30 minutes with stirring. Upon cooling to 0°–5° C. a precipitate forms which is separated by filtration and dried, yielding 5.4 g of 4-bromo-N-butyl-2-nitro-1-naphthylamine. An additional 0.92 g is recovered from the mother liquor and the two crops are combined together and recrystallized from methanol. M.p. 65°–66.5° C. A mixture of 17.6 g (0.0544 mole) of this compound and 7.84 cc (0.0816 mole) of 3-chloropropionyl chloride is stirred at 60° C. for four hours. When the reaction is completed the mixture is poured in a separatory funnel and vigorously shaken with methylene chloride and a 5% aqueous NaHCO$_3$ solution. The organic layer is separated, washed with water and dried. The residue which is obtained by evaporating off the methylene chloride is dissolved in 180 cc of EtOH and 22 cc of glacial acetic acid. 10.4 g of powdered iron is added to the obtained solution and the resulting mixture is refluxed with stirring for 20 minutes; then it is poured into 720 cc of water and extracted with methylene chloride. The methylene chloride is evaporated off, the residue is dissolved in a mixture of 125 cc of 95% EtOH and 50 cc of 10% HCl and heated at reflux temperature for 1½ hour. The solvent is boiled off and the solid residue is triturated with ether, filtered and dried. The yield in 5-bromo-1-butyl-2-(2-chloroethyl)-1H-naphth[1,2-d]imidazole, m.p. 172° C. (dec.), is 19.4 g (90.8%).

EXAMPLE 38

5-Bromo-1-(1-methylethyl)-2-(2-chloroethyl)-1H-naphth[1,2-d]imidazole

The compound of the title is prepared by following the procedure described in the foregoing example but using (1-methylethyl)amine instead of butylamine. The corresponding hydrochloride melts at 137° C. with decomposition (from ethanol).

EXAMPLE 39

2-(2-Chloroethyl)-naphth[1,2-d]oxazole 19.5 g (0.1 mole) of 1-hydroxy-2-naphthylamine hydrochloride and 10 cc (0.1 mole) of 3-chloro-propionyl chloride in 250 cc of polyphosphoric acid are stirred at room temperature for 3 hours. After standing at room temperature for two days, the reaction mixture is heated to 80° C. for 7 hours and to 100° C. for 1 hour, then it is poured into 2 liters of ice water. The product is extraacted with ethyl ether and purified by means of column chromatography (eluent cyclohexane:ethyl acetate 8:2). Yield 5.38 g. M.p. 80°–82° C.

EXAMPLE 40

2-(3-Chloropropyl)-1-methyl-1H-napth[1,2-d]imidazole 11.25 cc (0.08 mole) of triethylamine in 100 cc of anhydrous methylene chloride and 4.48 cc (0.04 mole) of 4-chlorobutanoyl chloride in 100 cc of methylene chloride are added dropwise to a methylene chloride solution of 8.78 g (0.04 mole) of $N^1$-methyl-1,2-naphthyldiamine hydrochloride, prepared as described in Example 36, cooled to 0°–5° C. and maintained under an argon atmosphere. When the addition, which takes about 90 minutes, is terminated the reaction mixture is allowed to stand at room temperature for 1 hour. Further, 1.15 cc (0.008 mole) of triethylamine and 0.45 cc (0.004 mole) of 4-chlorobutanoyl chloride are added and the mixture is stirred at room temperature, for 1 hour, washed with water and dried. The residue, obtained by evaporating the solvent, is taken up with 500 cc of 5% HCl and stirred at 60° C. for 3 hours and at 90° C. for further 30 minutes. By the addition of NH$_4$OH at room temperature, a precipitate forms which is separated by filtration and recrystallized from ethyl acetate. Yield 6 g. M.p. 246°–48° C.

EXAMPLE 41

5-Bromo-2-(2-Chloroethyl)-1-methyl-1H-naphth[1,2-d]imidazole

A mixture of 80.3 g (0.286 mole) of 4-bromo-N-methyl-2-nitro-1-naphthylamine, prepared as described in the first part of Example 36, and 41 cc (0.426 mole) of 3-chloropropanoyl chloride is stirred for 2 hours at 60° C. and for a further 2 hours at 80° C. The excess of acyl chloride is distilled off at 40° C. under vacuum and the residue, taken up with methylene chloride, is washed first with a saturated NaHCO$_3$ solution and then with water.

By evaporating the solvent, a residue is obtained which is purified by column chromatography (eluent-:cyclohexane:ethyl acetate 8:2). The obtained intermediate product is dissolved in 750 cc of absolute alcohol and reduced by means of powdered iron (47.8 g) in glacial acetic acid (98 cc). The mixture is stirred at reflux temperature for ½ hour under argon atmosphere then it is poured into 2500 cc of water ccontaining 1000 cc of glacial acetic acid and extracted with methylene chloride. The organic layer is dried over MgSO₄ and the solvent is distilled off. The residue is dissolved in 500 cc of 95% Ethanol and 200 cc of 10% HCl and refluxed for 1½ hours. Upon cooling the reaction mixture to room temperature, a precipitate forms (35 g) which is separated by filtration. The aqueous liquors are concentrated to a small volume and by the addition of 150 cc of acetone, a further crop (38 g) of 5-bromo-2-(2-chloroethyl)-1-methyl-1H-naphth[1,2-d]imidazole hydrochloride precipitates. The two combined crops are dissolved in methanol and the solution is made alkaline by the addition of 10% NaOH. By pouring it in water, the free base separates as a crystalline solid. M.p. 146°-148° C. (CH₃OH).

EXAMPLE 42

2-[2-Methyl-naphth[1,2-d]imidazole-1-yl]ethyl methanesulfonate 0.67 g (0.011 mole) of 2-aminoethanol is added to a solution of 2.82 g (0.01 mole) of 4-bromo-2-nitro-1-methoxy naphthalene in 20 cc of dimethylformamide and the obtained mixture is heated to 60° C. with stirring. After 1 hour, the reaction mixture is poured into ice water.

The precipitate which forms is filtered and dried, yielding 2.5 g (0.008 mole) of intermediate compound. This intermediate is mixed with 1.71 cc (0.024 mole) of acetyl chloride, and the mixture is refluxed for 30 minutes, and then taken up with 100 cc of ethyl ether. The organic solution, washed with a sodium bicarbonate solution and then with water, is dried over MgSO₄, filtered and concentrated to dryness, yielding 3.18 g. 2.5 g of the obtained compound is dissolved in 100 cc of methanol and 0.9 cc of triethylamine and catalytically hydrogenated at room temperature under about 5.4 atm. of hydrogen pressure in the presence of 0.5 g of 20% palladium adsorbed on charcoal. After 1 hour, the catalyst is filtered off and the solvent is evaporated.

The obtained residue is taken up with methylene chloride and is then washed with water. The organic layer is dried over MgSO₄, filtered and concentrated to dryness, yielding 1.9 g of intermediate product. 10.02 g (0.035 mole) of this intermediate compound and 6.65 g (0.035 mole) of toluenesulfonic acid hydrate are dissolved in 600 cc of toluene and the obtained solution is heated for 30 minutes at reflux temperature. After evaporating the solvent, the residue is taken up with a solution of 185 cc of 5% HCl in 300 cc of methaol and refluxed for one hour. The solvent is then evaporated to a volume of 250 cc and the solution is diluted with 1000 cc of ice water and made alkaline with 10% NaOH. The solid which precipitates is separated by filtration and dissolved in 830 cc of methylene chloride containing 6.48 cc of triethylamine.

A solution of 2.78 cc of methanesulfonyl chloride in 30 cc of methylene chloride is added over a period of 20 minutes to the methylene chloride solution cooled to 10° C. After stirring for 1 hour at 10° C., the reaction mixture is washed twice with 300 cc of water, dried and concentrated to dryness, yielding 8.9 g of the compound of the title. M.p. 169°-171° C. (95% EtOH).

We claim:
1. A compound of the formula

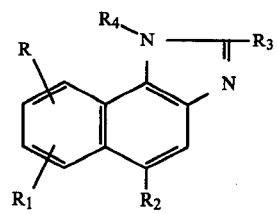

wherein R and R₁, each independently, are selected from the group consisting of hydrogen, halogen, ($C_1$–$C_6$) alkyl and ($C_1$–$C_6$) alkoxy; $R_2$ represents hydrogen or halogen; $R_3$ represents a —$(CH_2)_n$—$NR_5R_6$ group wherein n is 2 or 3 and $R_5$ and $R_6$ taken together with the adjacent nitrogen atom represent a piperazino moiety optionally having a substituent selected from the group consisting of ($C_1$–$C_6$) alkyl, ($C_2$–$C_6$) alkenyl, ($C_5$–$C_6$) cycloalkyl, lower alkanoyl of $C_2$–$C_6$ carbons, phenyl, phenyl substituted with 1 to 3 groups independently selected from ($C_1$–$C_6$) alkyl, ($C_1$–$C_6$) alkoxy, hydroxy, benzyloxy, halogen, trifluoromethyl, amino, mono- and di-alkylamino, pyridyl, benzyl and halobenzyl; $R_4$ represents hydrogen or ($C_1$–$C_6$) alkyl; or a non-toxic pharmaceutically-acceptable acid addition salt thereof.

2. The compound of claim 1 which is 1-(methylethyl)-2-[2-[4-(3-trifluoromethylphenyl)-1-piperazinyl]-ethyl]-1H-naphth[1,2-d]imidazole or a non-toxic pharmaceutically-acceptable acid addition salt thereof.

3. The compound of claim 1 which is the citrate salt.

* * * * *

UNITED STATES PATENT AND TRADEMARK OFFICE
CERTIFICATE OF CORRECTION

PATENT NO. : 4,461,894

DATED : July 24, 1984

INVENTOR(S) : Amedeo Omodei-Sale'; Emilio Toia

It is certified that error appears in the above-identified patent and that said Letters Patent is hereby corrected as shown below:

At Column 3, Line 56 Patent reads: "pufified" and should read: "purified".

At Column 9, Line 11 Patent reads: "phenylipiperazine" and should read: "phenylpiperazine".

At Column 13, Line 50 Patent reads: "lmethyl-2-" and should read: "1-methyl-2-".

Signed and Sealed this

Seventeenth Day of April, 1990

Attest:

HARRY F. MANBECK, JR.

*Attesting Officer*   *Commissioner of Patents and Trademarks*